United States Patent [19]

Findeisen et al.

[11] Patent Number: 5,051,517
[45] Date of Patent: Sep. 24, 1991

[54] PROCESS FOR THE PREPARATION OF HERBICIDALLY ACTIVE 3-AMINO-5-AMINOCARBONYL-1,2,4-TRIAZOLES

[75] Inventors: Kurt Findeisen, Odenthal; Markus Lindig, Hilden, both of Fed. Rep. of Germany

[73] Assignee: Bayer Aktiengesellschaft, Leverkusen, Fed. Rep. of Germany

[21] Appl. No.: 520,338

[22] Filed: May 7, 1990

[30] Foreign Application Priority Data

May 20, 1989 [DE] Fed. Rep. of Germany ....... 3916430

[51] Int. Cl.$^5$ .................. C07D 401/04; C07D 401/12; C07D 403/02; C07D 413/02
[52] U.S. Cl. ................................. 548/265.6; 540/603; 544/132; 544/366; 546/210; 546/276; 548/265.4
[58] Field of Search ................... 548/266, 265.4, 265.6; 540/603; 544/132, 366; 546/210, 276

[56] References Cited

U.S. PATENT DOCUMENTS 4,578,479  3/1986  Fukui et al. .......................... 548/269
5,021,081  6/1991  Findeisen ............................... 71/92

FOREIGN PATENT DOCUMENTS 0126326  11/1984  European Pat. Off. .
3709574  10/1988  Fed. Rep. of Germany .

OTHER PUBLICATIONS

Chemical Abstracts, vol. 63, No. 10, Nov. 8, 1965, Paragraph 13243f–13244b, Columbus, Ohio, U.S: G. E. Cipens et al.:"Derivatives of 1,2,4–triazole-5-carboxylic acid", & Latvijas PSR Zinatnu Akad. Vestis, Kim. Ser. 1965 (2), 294–298.
Bulletin De La Societe Chimique De France, No. 4, Apr. 1970, pp. 1590–1599, Paris, FR; M. Pesson et al.: "Recherches sur les derives du triazole-1,2,4. V.–Amides N–dialkyles d'acides triazol-1,2,4 yl-5 carboxyliques".
Findeisen et al., Chem. Abst. 112-139036r (1990).

Primary Examiner—Cecilia Shen
Attorney, Agent, or Firm—Sprung, Horn, Kramer & Woods

[57] ABSTRACT 3-amino-5-amino-carbonyl-1,2,4-triazoles of the formula

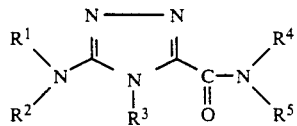

are obtained in good yields and in high purity when a chloroformadine hydrochloride of the formula

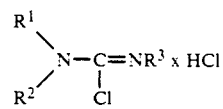

are reacted with an oxamohydrazide of the formula

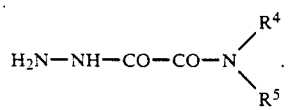

This reaction can be carried out in the presence of an acid acceptor and in the presence of a diluent at temperatures between 0° C. and 150° C.

7 Claims, No Drawings

PROCESS FOR THE PREPARATION OF HERBICIDALLY ACTIVE 3-AMINO-5-AMINOCARBONYL-1,2,4-TRIAZOLES

The invention relates to a new process for the preparation of 3-amino-5-aminocarbonyl-1,2,4-triazole derivatives, which, as new, herbicidally active substances, form the subject-matter of a previous, non-prior-published patent application (cf. German Patent Application 809,053, dated 18 Mar., 1988, corresponding to U.S.-application Ser. No. 324,361 filed Mar. 15, 1989 now U.S. Pat. No. 5,021,081.

From said patent application it can be seen that 3-amino-5-aminocarbonyl-1,2,4-triazole derivatives are obtained when (a) suitable aminoguanidines are reacted with oxalic ester amides or (b) suitable triazolyl carboxylic esters are reacted with amines. In many cases, both methods yield the 3-amino-5-aminocarbonyl-1,2,4-triazole derivatives only in unsatisfactory yields.

It has now been found that 3-amino-5-aminocarbonyl-1,2,4-triazole derivatives of the general formula (I)

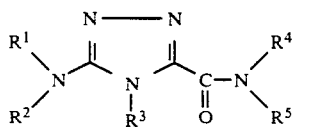

in which
R$^1$ and R$^2$ independently of one another each represent hydrogen, alkyl, alkenyl, alkinyl, halogenoalkyl, halogenoalkenyl, halogenoalkinyl, alkoxyalkyl, cycloalkyl or cycloalkylalkyl, or represent in each case optionally substituted aryl, aralkyl or heteroaryl, or together with the nitrogen atom to which they are bonded represent an optionally substituted heterocycle,
R$^3$ represents alkyl, alkenyl, alkinyl, halogenoalkyl, halogenoalkenyl, halogenoalkinyl, alkoxyalkyl, cycloalkylalkyl or cycloalkyl, or represents in each case optionally substituted aralkyl or aryl, and
R$^4$ and R$^5$ independently of one another each represent hydrogen, alkyl, alkenyl, alkinyl, halogenoalkyl, halogenoalkenyl, halogenoalkinyl, cyanoalkyl, hydroxyalkyl, alkoxyalkyl, alkylaminoalkyl, dialkylaminoalkyl, alkoximinoalkyl, alkoxycarbonylalkyl or alkoxycarbon-ylalkenyl, or represent in each case optionally substituted cycloalkyl, cycloalkylalkyl, cycloalkenyl or cycloalkenylalkyl, or represent optionally substituted heterocyclylalkyl, or represent in each case optionally substituted aralkyl, aroyl or aryl, or together with the nitrogen atom to which they are bonded represent an optionally substituted heterocycle, are obtained in good yields and in high purity when chloro-formamidine hydrochlorides of the general formula (II)

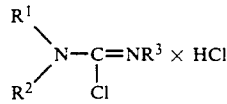

in which
R$^1$, R$^2$ and R$^3$ are as defined above are reacted with oxamohydrazides of the general formula (III)

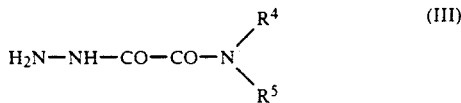

in which
R$^4$ and R$^5$ are as defined above in the presence of an acid acceptor and in the presence of a diluent at temperatures between 0° C. and 150° C.

Formula (I) provides a general definition of the substituted triazoles to be prepared according to the invention. Preferred compounds of the formula (I) are those in which
R$^1$ and R$^2$ independently of one another each represent hydrogen, or represent in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl, in each case having 2 to 8 carbon atoms and 1 to 15, or 13, identical or different halogen atoms, alkoxyalkyl having 1 to 6 carbon atoms in the individual alkyl moieties, or represent cycloalkyl having 3 to 7 carbon atoms, or represent cycloalkylalkyl having 3 to 7 carbon atoms in the cycloalkyl moiety and 1 to 6 carbon atoms in the straight-chain or branched alkyl moiety, or represent aralkyl which has 6 to 10 carbon atoms in the aryl moiety and 1 to 6 carbon atoms in the straight-chain or branched alkyl moiety and which is optionally monosubstituted or polysubstituted by identical or different substituents, aryl which has 6 to 10 carbon atoms and which is optionally monosubstituted or polysubstituted or heteroaryl which has 2 to 9 carbon atoms and 1 to 3 hetero atoms, in particular nitrogen, oxygen and/or sulphur and which is optionally monosubstituted or polysubstituted, suitable substituents in each case being: halogen, cyano, nitro and in each case straight-chain or branched alkyl, alkoxy, alkylthio, halogenoalkyl, halogenoalkoxy or halogenoalkylthio, in each case having 1 to 4 carbon atoms and if appropriate 1 to 9 identical or different halogen atoms, or
R$^1$ and R$^2$ together with the nitrogen atom to which they are bonded represent a five- to ten-membered heterocycle which can optionally contain 1 to 2 further hetero atoms, in particular nitrogen, oxygen and/or sulphur and which is optionally monosubstituted or polysubstituted by identical or different substituents, suitable substituents being: halogen, and in each case straight-chain or branched alkyl or halogenoalkyl, in each case having 1 to 4 carbon atoms and if appropriate 1 to 9 identical or different halogen atoms and 1 to 2 oxo or thiono groups,
R$^3$ represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, alkoxyalkyl having in each case 1 to 6 carbon atoms in the individual alkyl moieties, or represents cycloalkylalkyl or cycloalkyl, in each case having 3 to 7 carbon atoms in the cycloalkyl moiety and if appropriate 1 to 6 carbon atoms in the straight-chain or branched alkyl moiety, or represents aralkyl or aryl, each of which has 6 to 10 carbon atoms in the aryl moiety and if appropriate 1 to 6 carbon atoms in the straight-chain or branched alkyl moiety and each of which is optionally monosubstituted or polysubstituted by identical or different substituents, suitable aryl substituents in each case being: halogen, cyano, nitro and in each case straight-chain or branched alkyl, alkoxy, alkylthio, halogenoalkyl, halogenoalkoxy or halogenoalkylthio, in each case having 1 to 4 carbon atoms and if appropriate 1 to 9 identical or different halogen atoms, $R^4$ and $R^5$ independently of one another each represent hydrogen, or represent in each case straight-chain or branched alkyl having 1 to 18 carbon atoms, alkenyl having 2 to 8 carbon atoms, alkinyl having 2 to 8 carbon atoms, halogenoalkyl having 1 to 8 carbon atoms and 1 to 17 identical or different halogen atoms, or halogenoalkenyl or halogenoalkinyl, in each case having 2 to 8 carbon atoms and 1 to 15, or 13, identical or different halogen atoms, or cyanoalkyl having 1 to 8 carbon atoms, hydroxyalkyl having 1 to 8 carbon atoms and 1 to 6 hydroxyl groups, alkoxyalkyl, alkoximinoalkyl, alkoxycarbonylalkyl or alkoxycarbonylalkenyl, in each case having up to 6 carbon atoms in the individual alkyl or alkenyl moieties, or alkylaminoalkyl or dialkylaminoalkyl, in each case having 1 to 6 carbon atoms in the individual alkyl moieties, or cycloalkyl, cycloalkylalkyl, cycloalkenyl or cycloalkenylalkyl, each of which has 3 to 8 carbon atoms in the cycloalkyl or cycloalkenyl moiety and if appropriate 1 to 6 carbon atoms in the straight-chain or branched alkyl moiety and each of which is optionally monosubstituted or polysubstituted by identical or different substituents, suitable substituents in each case being: halogen, cyano, and in each case straight-chain or branched alkyl or halogenoalkyl, in each case having 1 to 4 carbon atoms and if appropriate 1 to 9 identical or different halogen atoms, or in each case double-linked alkanediyl or alkenediyl, in each case having up to 4 carbon atoms; $R^4$ and $R^5$ independently of one another furthermore represent heterocyclylalkyl which has 1 to 6 carbon atoms in the straight-chain or branched alkyl moiety and 1 to 9 carbon atoms as well as 1 to 3 hetero atoms—in particular nitrogen, oxygen and/or sulphur—in the heterocyclyl moiety and which is optionally monosubstituted or polysubstituted in the heterocyclyl moiety by identical or different substituents, suitable substituents being: halogen, cyano, nitro, and in each case straight-chain or branched alkyl, alkoxy, alkylthio, halogenoalkyl, halogenoalkoxy, halogenoalkylthio or alkoxycarbonyl, in each case having 1 to 5 carbon atoms and if appropriate 1 to 9 identical or different halogen atoms, $R^4$ and $R^5$ independently of one another furthermore represent aralkyl, aroyl or aryl, each of which has 6 to 10 carbon atoms in the aryl moiety and if appropriate 1 to 8 carbon atoms in the straight-chain or branched alkyl moiety and each of which is optionally monosubstituted or polysubstituted by identical or different substituents, suitable aryl substituents in each case being: halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl, in each case having 1 to 6 carbon atoms and if appropriate 1 to 9 identical or different halogen atoms, or cycloalkyl having 3 to 6 carbon atoms or phenoxy, and, if appropriate, suitable alkyl substituents being halogen or cyano, or $R^4$ and $R^5$ together with the nitrogen atom to which they are bonded represent a five- to ten-membered heterocycle which can optionally contain 1 to 2 further hetero atoms, in particular nitrogen, oxygen and/or sulphur, and which is optionally monosubstituted or polysubstituted by identical or different substituents, suitable substituents being: halogen, and in each case straight-chain or branched alkyl or halogenoalkyl, in each case having 1 to 4 carbon atoms and if appropriate 1 to 9 identical or different halogen atoms as well as 1 to 2 oxo or thiono groups.

Compounds of the formula (I) which are particularly preferably prepared by the process according to the invention are those in which $R^1$ and $R^2$ independently of one another each represent hydrogen, or represent methyl, ethyl, n- or i-propyl, n-, i-, s- or t-butyl, n- or i-pentyl, allyl or propargyl, or represent in each case straight-chain or branched halogenoalkyl having 1 to 4 carbon atoms, halogenoalkenyl having 3 to 6 carbon atoms or halogenoalkinyl having 3 to 6 carbon atoms and in each case 1 to 9 identical or different halogen atoms, or represent methoxymethyl or methoxyethyl, or represent cyclopropyl, cyclopropylmethyl, cyclopentyl, cyclohexyl, cyclohexylmethyl, cyclohexylethyl or cyclopentylmethyl, or represent benzyl, phenylethyl or phenyl, each of which is optionally monosubstituted to trisubstituted by identical or different substituents, suitable substituents being:

fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, or $R^1$ and $R^2$ together with the nitrogen atom to which they are bonded represent a heterocycle of the formula

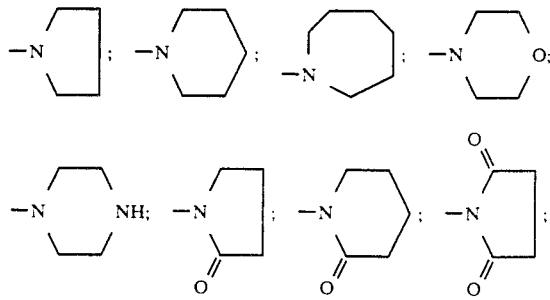

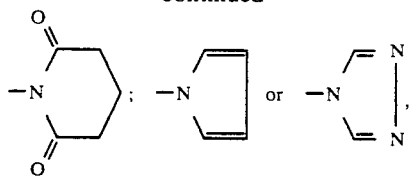
each of which is optionally monosubstituted to trisubstituted by identical or different substituents, suitable substituents in each case being: methyl, ethyl, n- or i-propyl, chlorine or trifluoromethyl, represents methyl, ethyl, n- or i-propyl, n-, i-, s- or t-butyl, n- or i-pentyl or n- or i-hexyl, or represents allyl or propargyl, or represents methoxymethyl, or represents straight-chain or branched halogenoalkyl having 1 to 4 carbon atoms and 1 to 9 identical or different halogen atoms, in particular fluorine, chlorine or bromine, or represents cyclopentyl, cyclohexyl, cyclopropyl, cyclopropylmethyl, cyclohexylmethyl or cyclohexylethyl, or represents benzyl or phenyl, each of which is optionally monosubstituted to trisubstituted by identical or different substituents, suitable substituents in each case being: fluorine, chlorine, bromine, cyano, t-butyl, methoxy, ethoxy, methylthio, trifluoromethyl, trifluoromethoxy or trifluoromethylthio, $R^4$ and $R^5$ independently of one another each represent hydrogen, methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl or n- or i-dodecyl, or represent allyl, n- or i-butenyl, n- or i-pentenyl, n- or i-hexenyl, propargyl, n- or i-butinyl, n- or i-pentinyl or n- or i-hexinyl, or represent straight-chain or branched halogenoalkyl having 1 to 6 carbon atoms and 1 to 9 identical or different halogen atoms, in particular fluorine, chlorine or bromine, or represent in each case straight-chain or branched halogenoalkenyl or halogenoalkinyl, in each case having 3 to 5 carbon atoms and 1 to 3 halogen atoms, in particular fluorine or chlorine, or represent in each case straight-chain or branched cyanoalkyl having 1 to 6 carbon atoms in the alkyl moiety, hydroxyalkyl having 1 to 6 carbon atoms and 1 to 3 hydroxyl groups, alkoxyalkyl, alkoximinoalkyl, alkoxycarbonylalkyl or alkoxycarbonylalkenyl, alkylaminoalkyl or dialkylaminoalkyl, in each case having up to 4 carbon atoms in the individual alkyl or alkyenyl moieties, or represent cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl, cyclohexenylmethyl or cyclohexenylethyl, each of which is optionally monosubstituted to trisubstituted by identical or different substituents, suitable substituents in each case being: fluorine, chlorine, bromine, methyl, ethyl, n- or i-propyl, n-, i-, s- or t-butyl, cyano, methanediyl, ethanediyl, butanediyl or butadienediyl;

$R^4$ and $R^5$ independently of one another furthermore represent heterocyclylmethyl, heterocyclylpropyl or heterocyclylethyl, suitable heterocycles in each case being:

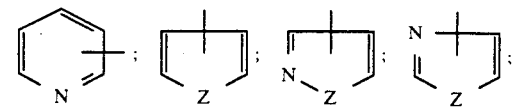
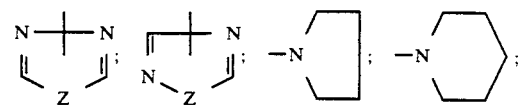
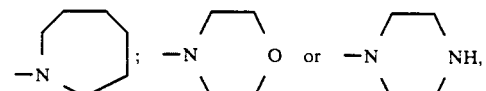

Z in each case representing oxygen or sulphur, each of which is optionally monosubstituted to trisubstituted in the heterocyclyl moiety by identical or different substituents, suitable substituents in each case being:
 fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio; $R^4$ and $R^5$ independently of one another furthermore represent benzyl, phenylethyl, phenylpropyl, phenylbutyl, phenylpentyl, phenylhexyl, phenylheptyl, phenylcyanomethyl, phenylcyanoethyl, phenylcyanopropyl, benzoyl, phenyl or naphthyl, where appropriate straight-chain or branched and in each case optionally monosubstituted to trisubstituted by identical or different substituents, suitable phenyl substituents in each case being: fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trilfuoromethylsulphinyl, trifluoromethylsulphonyl, methylsulphinyl, methylsulphonyl, acetyl, propionyl, methoxycarbonyl, ethoxycarbonyl, cyclohexyl or phenoxy, or $R^4$ and $R^5$ together with the nitrogen atom to which they are bonded represent a heterocycle of the formula

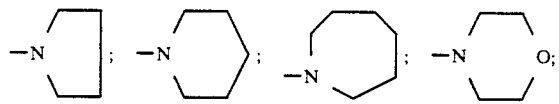
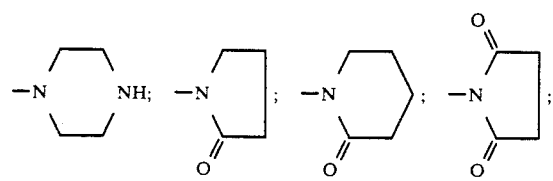
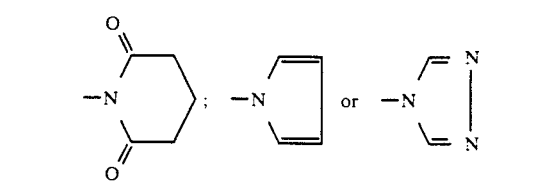

which is optionally monosubstituted to trisubstituted by identical or different substituents, suitable substituents in each case being; methyl, ethyl, n- or i-propyl, chlorine or trifluoromethyl.

Compounds of the formula (I) which are very particularly preferably prepared by the process according to the invention are those in which $R^1$ represents hydrogen, methyl or ethyl,
$R^2$ represents methyl or ethyl,
$R^3$ represents methyl or ethyl,
$R^4$ represents hydrogen or methyl,
$R^5$ represents hydrogen, methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl or n- or i-dodecyl, or represents allyl, n- or i-butenyl, n- or i-pentenyl, n- or i-hexenyl, propargyl, n- or i-butinyl, n- or i-pentinyl or n- or i-hexinyl, or represents straight-chain or branched halogenoalkyl having 1 to 6 carbon atoms and 1 to 9 identical or different halogen atoms, in particular fluorine, chlorine or bromine, or represents in each case straight-chain or branched halogenoalkenyl or halogenoalkinyl, in each case having 3 to 5 carbon atoms and 1 to 3 halogen atoms, in particular fluorine and/or chlorine, or represents in each case straight-chain or branched cyanoalkyl having 1 to 6 carbon atoms in the alkyl moiety, hydroxyalkyl having 1 to 6 carbon atoms and 1 to 3 hydroxyl groups, or alkoxyalkyl, alkoximinoalkyl, alkoxycarbonylalkyl or alkoxycarbonylalkenyl, alkylaminoalkyl or dialkylaminoalkyl, in each case having up to 4 carbon atoms in the individual alkyl or alkenyl moieties, or represents cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl, cyclohexenylmethyl or cyclohexenylethyl, each of which is optionally monosubstituted to trisubstituted by identical or different substituents from the series comprising fluorine, chlorine, bromine, methyl, ethyl, n- or i-propyl, n-, i-, s- or t-butyl, cyano, methanediyl, ethanediyl, butanediyl or butadienediyl;

$R^5$ furthermore represents heterocyclylmethyl, heterocyclylpropyl or heterocyclylethyl, suitable heterocycles in each case being:

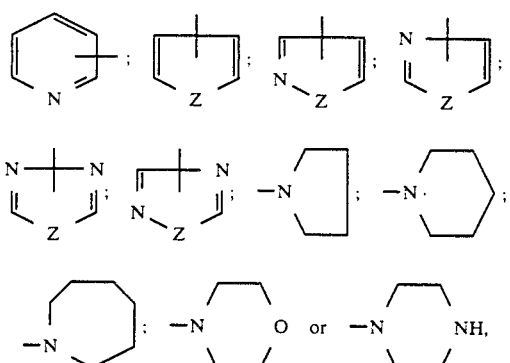

where Z in each case represents oxygen or sulphur and each of which is optionally monosubstituted to trisubstituted in the heterocyclyl moiety by identical or different substituents from the series comprising fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, $R^5$ furthermore represents benzyl, phenylethyl, phenylpropyl, phenylbutyl, phenylpentyl, phenylhexyl, phenylheptyl, phenylcyanomethyl, phenylcyanoethyl, phenylcyanopropyl, benzoyl, phenyl or naphthyl, if appropriate straight-chain or branched and in each case optionally monosubstituted to trisubstituted in the phenyl moiety by identical or different substituents from the series comprising fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl or phenoxy.

Compounds of the formula (I) which are prepared by the process according to the invention are, in particular, those in which $R^1$, $R^2$, $R^3$ and $R^4$ have the meaning indicated above as being very particularly preferred and $R^5$ is hydrogen, methyl, ethyl, n- or i-propyl, n-, i-, s- or t-butyl, n- or i-pentyl, n- or i-hexyl, allyl, n- or i-butenyl, n- or i-pentenyl, propgargyl, n- or i-butinyl, n- or i-pentinyl, halogeno-$C_1$-$C_6$-alkyl having 1 to 6 identical or different halogen atoms, in particular fluorine and chlorine, halogeno-$C_3$-$C_5$-alkenyl or halogeno-$C_3$-$C_5$-alkinyl, in each case having 1 to 3 halogen atoms, in particular fluorine and/or chlorine, or cyclopropyl, cyclopentyl, cyclohexyl, cyclopropylmethyl, cyclopentylmethyl or cyclohexylmethyl, in each case optionally monosubstituted to trisubstituted by identical or different substituents, fluorine, chlorine, bromine, methyl and ethyl being chosen as the substituents.

In addition to the compounds mentioned in the Preparation Examples, the following compounds of the general formula (I) may be mentioned individually:

$$\begin{array}{c} R^1 \\ \diagdown \\ N \\ / \\ R^2 \end{array} \begin{array}{c} N \!=\!\!=\! N \\ \| \\ \diagdown \\ N \\ | \\ R^3 \end{array} \begin{array}{c} \\ \\ C\!-\!N \\ \| \\ O \end{array} \begin{array}{c} R^4 \\ \diagup \\ \\ \diagdown \\ R^5 \end{array} \quad (I)$$

| $R^1$ | $R^2$ | $R^3$ | $R^4$ | $R^5$ |
|---|---|---|---|---|
| $CH_3$ | $CH_3$ | $C_2H_5$ | H | $-C(CH_3)_3$ |
| H | $CH_3$ | $CH_3$ | H | ⟨cyclohexyl⟩-H |
| H | $CH_3$ | $C_2H_5$ | H | $-CH_2-C(CH_3)_3$ |
| H | $CH_3$ | $C_2H_5$ | H | $-CH(CH_3)-$phenyl |
| $CH_3$ | $CH_3$ | $CH_3$ | $CH_3$ | $-C(CH_3)_3$ |
| $CH_3$ | $CH_3$ | $C_2H_5$ | $CH_3$ | $-C(CH_3)_3$ |
| $C_2H_5$ | $C_2H_5$ | $CH_3$ | H | $-C(CH_3)(CF_3)(CH_3)$ |
| H | $C_2H_5$ | $CH_3$ | H | $-C(CH_3)_3$ |
| H | $CH_3$ | $CH_3$ | $CH_3$ | $-C(CH_3)_3$ |

-continued

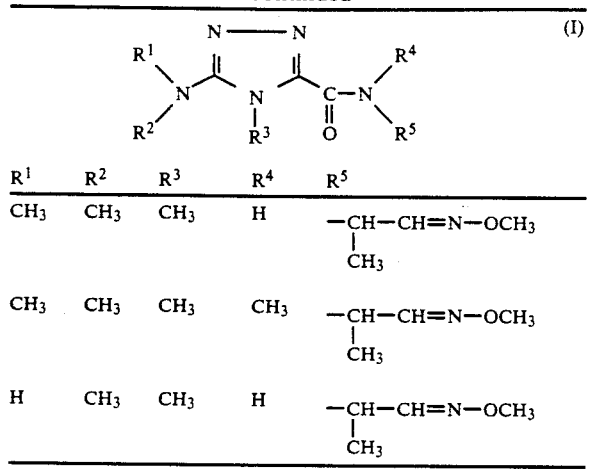

| R¹ | R² | R³ | R⁴ | R⁵ |
|---|---|---|---|---|
| CH₃ | CH₃ | CH₃ | H | —CH—CH=N—OCH₃<br>\|<br>CH₃ |
| CH₃ | CH₃ | CH₃ | CH₃ | —CH—CH=N—OCH₃<br>\|<br>CH₃ |
| H | CH₃ | CH₃ | H | —CH—CH=N—OCH₃<br>\|<br>CH₃ |

If, for example, chlorotrimethylformamidine hydrochloride and (N-methyloxamoyl)hydrazine are used as the starting substances, the course of the reaction in the process according to the invention can be represented by the following equation:

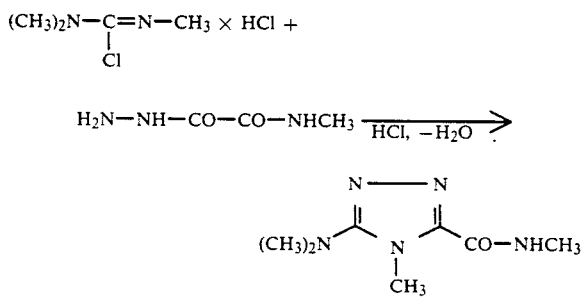

Formula (II) provides a general definition of the chloro-formamidine hydrochlorides to be used as starting substances in the process according to the invention for the preparation of compounds of the formula (I).

In formula (II), $R^1$, $R^2$ and $R^3$ preferably, or in particular, have those meanings which have already been mentioned above in connection with the description of the compounds of the formula (I) according to the invention as being preferred, or particularly preferred, for $R^1$, $R^2$ and $R^3$.

Examples of the starting substances of the formula (II) which may be mentioned are:

Chloro-N,N'-dimethyl-formamidine hydrochloride, chloro-N,N,N'-trimethyl-formamidine hydrochloride, chloro-N,N,N'-triethyl-formamidinehydrochloride, chloro-N,N,N'-tripropyl-formamidine hydrochloride, chloro-N,N,N'-triisopropyl-formamidine hydrochloride, chloro-N,N,N'-tributyl-formamidine hydrochloride, chloro-N,N-dimethyl-N'-ethyl-formamidine hydrochloride, chloro-N,N-dimethyl-N'-propyl-formamidine hydrochloride, chloro-N,N-dimethyl-N'-isopropyl-formamidine hydrochloride, chloro-N,N-dimethyl-N'-butyl-formamidine hydrochloride, chloro-N,N-dimethyl-N'-isobutyl-formamidine hydrochloride, chloro-N,N-dimethyl-N'-sec-butyl-formamidine hydrochloride, chloro-N,N-dimethyl-N'-tert-butyl-formamidine hydrochloride, chloro-N,N-diethyl-N'-methyl-formamidine hydrochloride, chloro-N,N-diethyl-N'-propyl-formamidine hydrochloride, chloro-N,N-diethyl-N'-butyl-formamidine hydrochloride, chloro-N,N-dipropyl-N'-methyl-formamidine hydrochloride and chloro-N,N-dipropyl-N'-ethyl-formamidine hydrochloride.

The starting substances of the formula (II) are known and/or can be prepared by processes known per se (cf. DE-OS (German Published Specification) 3,709,574; Chem. Ber. 97 (1964), 1232–1245).

Formula (III) provides a general definition of the oxamohydrazides also to be used as starting substances in the process according to the invention.

In formula (III), $R^4$ and $R^5$ preferably, or in particular, have those meanings which have already been mentioned above in connection with the description of the compounds of the formula (I) according to the invention as being preferred, or particularly preferred, for $R^4$ and $R^5$.

Starting substances of the formula (III) which may be mentioned are: (N-methyloxamoyl)hydrazine, (N-ethyloxamoyl)hydrazine, (N-propyloxamoyl)hydrazine, (N-isopropyloxamoyl)hydrazine, (N-butyloxamoyl)hydrazine, (N-isobutyloxamoyl)hydrazine, (N-sec-butyloxamoyl)hydrazine, (N-tert-butyloxamoyl)hydrazine, (N-pentyloxamoyl)hydrazine, (N-isopentyloxamoyl)hydrazine, (N-secpentyloxamoyl)hydrazine, (N-tert-pentyloxamoyl)hydrazine, (N-hexyloxamoyl)hydrazine, (N-isohexyloxamoyl)hydrazine, (N-octyloxamoyl)hydrazine, (N-2-fluoro-ethyloxamoyl)hydrazine, (N-2-chloro-ethyloxamoyl)hydrazine, (N-2,2,2-trifluoro-ethyloxamo-yl)hydrazine, [N-1,1-bis(fluoromethyl)ethyloxamoyl]hydrazine, (N-1,1-dimethyl-2,2,2-trifluoro-ethyloxamoyl)hydrazine, (N-1-cyano-2,2-dimethyl-propyloxamoyl)hydrazine, (N-2-cyano-ethyloxamoyl)hydrazine, (N-allyloxamoyl)hydrazine, (N-crotyloxamoyl)hydrazine, (N-propargyloxamoyl)hydrazine, (N-1-methyl-propargyloxamoyl)hydrazine, (N-1,1-dimethylpropargyloxamoyl)hydrazine, (N-cyclopropyloxamoyl)hydrazine, (N-1-methyl-cyclopropyloxamoyl)hydrazine, (N-cyclobutyloxamoyl)hydrazine, (N-1-methyl-cyclobutyloxamoyl)hydrazine, (N-cyclopentyloxamoyl)hydrazine, (N-1-methylcyclopentyloxamoyl)hydrazine, (N-cyclohexyloxamoyl)hydrazine, (N-1-methyl-cyclohexyloxamoyl)hydrazine, (N-2-methyl-cyclohexyloxamoyl)hydrazine, (N-3-methyl-cyclohexyloxamoyl)hydrazine, (N-4-methyl-cyclohexyloxamoyl)hydrazine, (N-benzyloxamoyl)hydrazine, (N-4-methyl-benzyloxamoyl)hydrazine, (N-1-phenyl-ethyloxamoyl)hydrazine, (N-2-phenyl-ethyl-oxamoyl)hydrazine and (N-1-cyano-1-methyl-propyloxamoyl)hydrazine.

The starting substances of the formula (III) are known and/or can be prepared by processes known per se (cf. EP-A 126,326 corresponding to U.S. Pat. No. 4,578,479).

The process according to the invention is carried out in the presence of a diluent. Diluents which are preferably employed are polar organic solvents and/or water. Preferred organic solvents are alcohols, such as methanol, ethanol, propanol, isopropanol and butanol, ethers, such as ethylene glycol dimethyl ether, diethylene glycol dimethyl ether, tetrahydrofuran and dioxane, ether alcohols, such as ethylene glycol monomethyl ether and ethylene glycol monoethyl ether, amides, such as formamide and dimethylformamide, nitriles, such as acetonitrile, propionitrile or benzonitrile, and also pyridine. Methanol is particularly preferred as the diluent.

Acid acceptors which can be employed in the process according to the invention are all acid-binding agents which can customarily be used for reactions of this type. The following are preferably suitable: alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate, potassium carbonate, sodium tert-butoxide and potassium tert-butoxide, furthermore aliphatic, aromatic trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]- octane (DABCO).

In the process according to the invention, the reaction temperatures can be varied within a substantial range. In general, the process is carried out at temperatures between 0° C. and 150° C., preferably at temperatures between 10° C. and 100° C.

In general, the process according to the invention is carried out under atmospheric pressure. However, it is also possible to carry out the process under increased or reduced pressure.

For carrying out the process according to the invention, between 0.5 and 1.5 moles, preferably between 0.8 and 1.2 moles, of oxamohydrazide of the formula (III) and between 1 and 5 mole equivalents, preferably between 2 and 3 mole equivalents, of an acid acceptor are generally employed per mole of chloroformamidine hydrochloride of the formula (II).

In general, the reactants of the formula (II) and (III) are mixed with the diluent at room temperature, an acid acceptor is added, and the mixture is stirred—if appropriate at increased temperature—until the reaction is complete.

The mixture can be worked up by customary methods.

When the reaction is complete, the reaction mixture is generally concentrated, and the residue is shaken with water and an organic solvent which is virtually water-immiscible, such as, for example, methylene chloride. The organic phase is separated off, dried with a drying agent, such as, for example, magnesium sulphate, and filtered. The solvent is carefully removed from the filtrate by distillation under a water pump vacuum. The residue which remains contains essentially the product of the formula (I), which can be purified further in a customary manner, for example by recrystallization.

PREPARATION EXAMPLES

Example 1

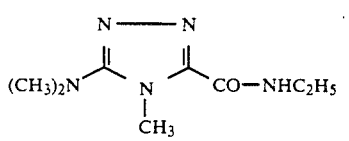

13.1 g (0.1 mol) of (N-ethyloxamoyl) hydrazine are added at 20° C. to a mixture of 18.8 g (0.12 mol) of chlorotrimethylformamidine hydrochloride and 300 ml of methanol. After 30.3 g (0.3 mole) of triethylamine have been added, the internal temperature rises to 44° C. The reaction mixture is refluxed for one hour and then concentrated under a water pump vacuum. The residue is shaken with methylene chloride/water, and the organic phase separated off, dried with sodium sulphate and filtered. The solvent is carefully removed from the filtrate by distillation under a water pump vacuum.

This gives 12.8 g (65 % of theory) of N-ethyl-5-dimethylamino-4-methyl-4H-1,2,4-triazol-3-yl-carboxamide as a crystalline residue of melting point 73° C.–75° C.

Example 2

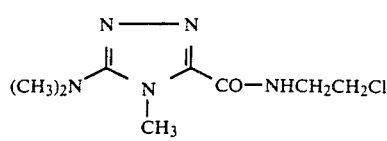

16.65 g (0.1 mol) of [N-(2-chloro-ethyl)-oxamoyl]hydrazine are added at 20° C. to a mixture of 18.8 g (0.12 mol) of chlorotrimethylformamidine hydrochloride and 300 ml of methanol. After 16.2 g (0.3 mol) of sodium methoxide have been added, the internal temperature rises to 62° C. The reaction mixture is stirred for one hour without further heating and then concentrated under a water pump vacuum. The residue is shaken with methylene chloride/water, and the organic phase is separated off, dried with magnesium sulphate and filtered. The solvent is carefully removed from the filtrate by distillation under a water pump vacuum.

This gives 18.5 g (80 % of theory) of N-(2-chloroethyl)-5-dimethylamino-4-methyl-4H-1,2,4-triazol3-yl-carboxamide as a crystalline residue of melting point 153° C.–155° C.

Example 3

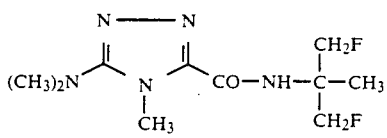

In analogy to Example 2, 19.5 g (0.1 mol) of [N-1,1-bis(fluoromethyl)-ethyloxamoyl]hydrazine and 18.8 g (0.12 mol) of chlorotrimethylformamidine hydrochloride give 19.7 g (75.5 % of theory) of N-1,1-bis(-fluoromethyl)ethyl-5-dimethylamino-4-methyl-4H-1,2,4-triazol-3-yl-carboxamide.

$^1$H-NMR (CDCl$_3$, δ, ppm): 1.55; 2.9; 4.5–4.8.

Example 4

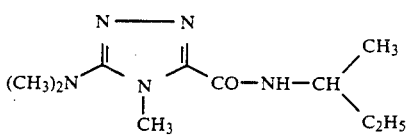

In analogy to Example 2, 11.0 g (0.067 mol) of (N-sec-butyloxamoyl)hydrazine and 10.8 g (0.069 mol) of chlorotrimethylformamidine hydrochloride give 12.0 g (80 % of theory) of N-sec-butyl-5-dimethylamino-4-methyl-4H-1,2,4-triazol-3-yl-carboxamide of boiling point 149°–152° C. (at 0.1 mbar).

$^1$H-NMR (CDCl$_3$, δ, ppm): 1.20–1.25; 2.85; 3.95–4.07.

Example 5

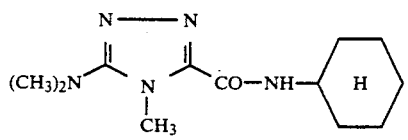

In analogy to Example 2, 13.8 g (0.074 mol) of (N-cyclohexyloxamoyl)hydrazine and 14.1 g (0.09 mol) of chlorotrimethylformamidine hydrochloride give 16.0 g (86 % of theory) of N-cyclohexyl-5-dimethylamino-4-methyl-4H-1,2,4-triazol-3-yl-carboxamide of melting point 60° C.–62° C.

Example 6

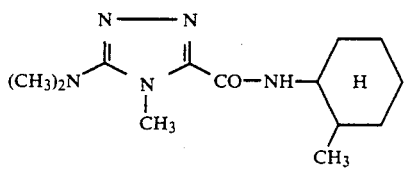

In analogy to Example 2, 10.0 g (0.05 mol) of [N-(2-methyl-cyclohexyl)-oxamoyl]hydrazine and 9.42 g (0.06 mol) of chlorotrimethylformamidine hydrochloride give 11.2 g (84.5 % of theory) of N-(2-methyl-cyclohexyl)-5-dimethylamino-4-methyl-4H-1,2,4-triazol-3-yl-carboxamide.

$^1$H-NMR (CDCl$_3$, δ, ppm): 0.90–0.95; 2.85.

Example 7

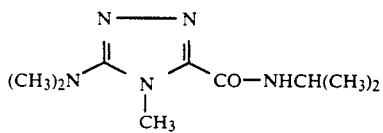

16.2 g (0.3 mol) of sodium methoxide are added to a stirred mixture of 18.8 g (0.12 mol) of chlorotrimethylformamidine hydrochloride, 14.5 g (0.10 mol) of (N-isopropyloxamoyl)hydrazine and 200 ml of methanol, and the reaction mixture is refluxed for 2 hours. After cooling, solids are filtered off with suction, the filtrate is concentrated, and the residue is shaken with methylene chloride/water. The organic phase is separated off, dried with sodium sulphate and filtered. The filtrate is worked up by distillation in vacuo.

This gives 16.0 g (76 % of theory) of N-isopropyl-5-dimethylamino-4-methyl-4H-1,2,4-triazol-3-yl-carboxamide of boiling point 133°–135° C. (at 0.1 mbar).

$^1$H-NMR (CDCl$_3$, δ, ppm): 1.25; 4.2; 7.3.

What is claimed is:

1. A process for the preparation of a 3-amino-5-aminocarbonyl- 1,2,4-triazole of the formula

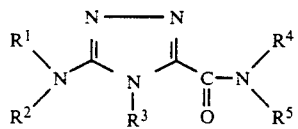

in which $R^1$ and $R^2$ independently of one another each represent hydrogen; alkyl having 1 to 8 carbon atoms; alkenyl having 2 to 8 carbon atoms; alkinyl having 2 to 8 carbon atoms; halgenoalkyl having 1 to 8 carbon atoms and 1 to 17 identical or different halogen atoms; halogenoalkenyl having 2 to 8 carbon atoms and 1 and 15 identical or different halogen atoms; halogenoalkinyl having 2 to 8 carbon atoms and 1 to 13 identical or different halogen atoms; alkoxyalkyl having 1 to 6 carbon atoms in the individual alkyl moieties; cycloalkyl having 3 to 7 carbon atoms; cycloalkylalkyl having 3 to 7 carbon atoms in the cycloalkyl moiety and 1 to 6 carbon atoms in the alkyl moiety; aralkyl which has 6 to 10 carbon atoms in the aryl moiety and 1 to 6 carbon atoms in the straight-chain or branched alkyl moiety and which is unsubstituted or substituted by identical or different substituents; aryl which has 6 to 10 carbon atoms and which is unsubstituted or substituted by identical or different substituents; or represents heteroaryl which has 2 to 9 carbon atoms and 1 and 3 identical or different nitrogen, oxygen and sulfur atoms and which is unsubstituted or substituted by identical or different substituents; and aralkyl, aryl and heteroaryl substituents being selected from the group consisting of halogen, cyano, nitro, and alkyl, alkoxy and alkylthio having in each case 1 to 4 carbon atoms, and halogenoalkyl, halogenoalkoxy, and halogenoalkylthio having in each case 1 to 4 carbon atoms and 1 to 9 identical or different halogen atoms; or $R^1$ and $R^2$ together with the nitrogen atom to which they are bonded also represents a five- to ten-membered heterocycle which optionally contains 1 to 2 further identical or different nitrogen, oxygen and sulphur atoms and which is unsubstituted or substituted by identical of different substituents selected from the group consisting of halogen, alkyl having 1 to 4 carbon atoms, halogenoalkyl having 1 to 4 carbon atoms and 1 to 9 identical or different halogen atoms, 1 or 2 oxo groups, or 1 or 2 thiono groups;

$R^3$ represents alkyl having 1 to 8 carbon atoms; alkenyl having 2 to 8 carbon atoms; alkinyl having 2 to 8 carbon atoms; halogenoalkyl having 1 to 8 carbon atoms and 1 to 17 identical or different halogen atoms; halogenoalkenyl having 2 to 8 carbon atoms and 1 to 15 identical or different halogen atoms; halogenoalkinyl having 2 to 8 carbon atoms and 1 and 13 identical or different halogen atoms; alkoxyalkyl having 1 to 6 carbon atoms in the individual alkyl moieties; cycloalkyl having 3 to 7 carbon atoms; cycloalkylalkyl having 3 to 7 carbon atoms in the cycloalkyl moiety and 1 and 6 carbon atoms in the alkyl moiety; aralkyl which has 6 to 10 carbon atoms in the aryl moiety and 1 to 6 carbon atoms in the alkyl moiety and which is unsubstituted or substituted by identical or different substituents; aryl which has 6 to 10 carbon atoms and which is unsubstituted or substituted by identical or different substituents; said aralkyl and aryl substituents being selected from the group consisting of halogen, cyano, nitro, and alkyl, alkoxy and alkylthio having in each case 1 to 4 carbon atoms, and halogenoalkyl, halogenoalkoxy, and halogenoalkylthio having in each case 1 to 4 carbon atoms and 1 to 9 identical or different halogen atoms;

$R^4$ and $R^5$ independently of one another each represent hydrogen; alkyl having 1 to 18 carbon atoms;

alkenyl having 2 to 8 carbon atoms; alkinyl having 2 to 8 carbon atoms; halgenoalkyl having 1 to 8 carbon atoms and 1 to 17 identical or different halogen atoms; halogenoalkenyl having 2 to 8 carbon atoms and 1 to 15 identical or different halogen atoms; halogenoalkinyl having 2 to 8 carbon atoms and 1 to 13 identical or different halogen atoms; cyanoalkyl having 1 to 8 carbon atoms; hydroxyalkyl having 1 to 8 carbon atoms and 1 to 6 hydroxyl groups; alkoxyalkyl, alkoximinoalkyl, alkoxycarbonylalkyl, or alkoxycarbonylalkenyl in each case having up to 6 carbon atoms in the individual alkyl or alkenyl moieties; alkylaminoalkyl or dialkylamino in each case having 1 to 6 carbon atoms in the individual alkyl moieties; cycloalkyl having 3 to 8 carbon atoms and which is unsubstituted or substituted by identical or different substituents; cycloalkylalkyl having 3 to 8 carbon atoms in the cycloalkyl moiety and 1 to 6 carbon atoms in the alkyl moiety and which is unsubstituted or substituted by identical or different substituents; cycloalkenyl having 3 to 8 carbon atoms and which is unsubstituted or substituted by identical or different substituents; or cycloalkenylalkyl having 3 to 8 carbon atoms in the cycloalkenyl moiety and 1 to 6 carbon atoms in the alkyl moiety and which is unsubstituted or substituted by identical or different substituents; said cycloalkyl, cycloalkylalkyl, cycloalkenyl, and cycloalkenylalkyl substituents being selected from the group consisting of halogen, cyano, alkyl having 1 to 4 carbon atoms, halogenoalkyl having 1 to 4 carbon atoms and 1 to 9 identical or different halogen atoms, double-linked alkanediyl having up to 4 carbon atoms, and double-linked alkenediyl having up to 4 carbon atoms; heterocyclylalkyl having 1 to 6 carbon atoms in the alkyl moiety and 1 to 9 carbon atoms and 1 to 3 hetero atoms in the heterocyclyl moiety and which is unsubstituted or substituted in the heterocyclyl moiety by identical or different substituents selected from the group consisting of halogen, cyano, nitro, and alkyl, alkoxy, alkylthio, and alkoxycarbonyl having in each case 1 to 5 carbon atoms, and halogenoalkyl, halogenoalkoxy, and halogenoalkylthio having in each case 1 to 5 carbon atoms and 1 to 9 identical or different halogen atoms; aralkyl having 6 to 10 carbon atoms in the aryl moiety and 1 to 8 carbon atoms in the alkyl moiety and which is unsubstituted or substituted in the aryl and alkyl moieties by identical or different substituents; aroyl or aryl each of which has 6 to 10 carbon atoms in the aryl moiety and which is unsubstituted or substituted in the aryl moiety by identical or different substituents; said aryl moiety substituents being selected from the group consisting of halogen, cyano, nitro, and alkyl, alkoxy, alkylthio, alkylsulphinyl, alkylsulphonyl, alkanoyl or alkoxycarbonyl having in each case 1 to 6 carbon atoms and halogenoalkyl, halogenoalkoxy, halogenoalkylthio, halogenoalkylsulphinyl and halogenoalkylsulphonyl having in each case 1 to 6 carbon atoms and 1 to 9 identical or different halogen atoms, and cycloalkyl having 3 to 6 carbon atoms, and phenoxy; and said alkyl moiety substituents being selected from the group consisting of halogen and cyano; or $R^4$ and $R^5$ together with the nitrogen atom to which they are bonded also represent a five- to ten-membered heterocycle which optionally contains 1 to 2 further hetero atoms and which is unsubstituted or substituted by identical or different substituents selected from the group consisting of halogen, alkyl having 1 to 4 carbon atoms, halogenoalkyl having 1 to 4 carbon atoms and 1 to 9 identical or different halogen atoms, 1 or 2 oxo groups, or 1 or 2 thiono groups;

comprising reaction a chloroformidine hydrochloride of the formula

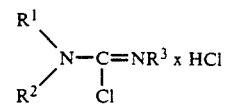

with an oxamohydrazide of the formula

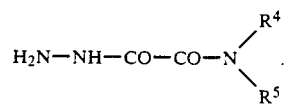

2. A process according to claim 1, in which
$R^1$ and $R^2$ independently of one another each represent hydrogen, or represent methyl, ethyl, n- or i-propyl, n-, i-, s- or t-butyl, n-or i-pentyl, allyl or propargyl, or represent halogenoalkyl having to 4 carbon atoms, halogenoalkenyl having 3 to 6 carbon atoms or halogenoalkinyl having 3 to 6 carbon atoms and in each case 1 to 9 identical or different halogen atoms, or represent methoxymethyl or methoxyethyl, or represent cyclopropyl, cyclopropylmethyl, cyclopentyl, cyclohexyl, cyclohexylmethyl, cyclohexylethyl or cyclopentylmethyl, or represent benzyl, pentylethyl or phenyl, each of which is unsubstituted or substituted by identical or different substituents, suitable substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, or $R^1$ and $R^2$ together with the nitrogen atom to which they are bonded can represent a heterocycle of the formula

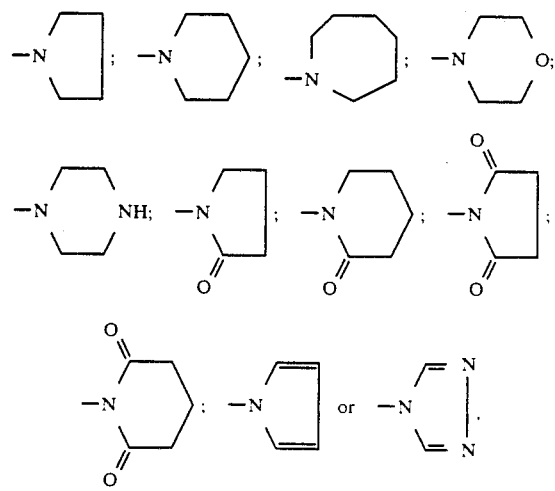

each of which is unsubstituted or substituted by identical or different substituents, suitable substituents in each case being: methyl, ethyl, n- or i-propyl, chlorine or trifluoromethyl, $R^3$ represents methyl, ethyl, n- or i-propyl, n-, i-, s-or t-butyl, n- or i-pentyl or n- or i-hexyl, or represents allyl or propargyl, or represents methoxymethyl, or represents halogenoalkyl having 1 to 4 carbon atoms and 1 to 9 identical or different halogen atoms, or represents cyclopentyl, cyclohexyl, cyclopropyl, cyclopropylmethyl, cyclohexylmethyl or cyclohexylethyl, or represents benzyl or phenyl, each of which is unsubstituted or substituted by identical or different substituents, suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, $R^4$ and $R^5$ independently of one another each present hydrogen, methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl or n- or i-dodecyl, or represent allyl, n- or i-butenyl, n- or i-pentenyl, n- or i-hexenyl, propargyl, n- or i-butinyl, n- or i-pentinyl or n- or i-hexinyl, or represent halogenoalkyl having 1 to 6 carbon atoms and to 9 identical or different halogen atoms, halogenoalkenyl or halogenoalkinyl, in each case having 3 to 5 carbon atoms and 1 to 3 halogen atoms, or represent cyanoalkyl having 1 to 6 carbon atoms in the alkyl moiety, hydroxyalkyl having 1 to 6 carbon atoms and 1 to 3 hydroxyl groups, alkoxyalkyl, alkoximinoalkyl, alkoxicarbonylalkyl or alkoxycarbonylalkenyl, alkylaminoalkyl or dialkylaminoalkyl, in each case having up to 4 carbon atoms in the individual alkyl or alkenyl moieties, or represent cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl, cyclohexenylmethyl or cyclohexenylethyl, each of which is unsubstituted or substituted by identical or different substituents, suitable substituents in each case being: fluorine, chlorine, bromine, methyl, ethyl, n- or i-propyl, n-, i-, s- or t-butyl, cyano, methanediyl, ethanediyl, butanediyl or butadienediyl;

$R^4$ and $R^5$ independently of one another furthermore represent heterocyclylmethyl, heterocyclylpropyl or heterocyclylethyl, suitable heterocycles in each case being:

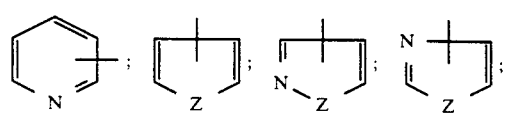

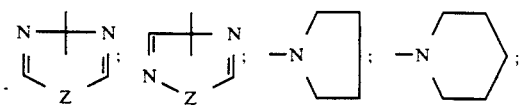

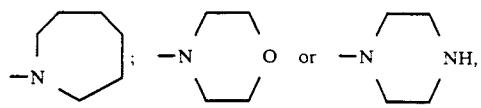

Z in each case representing oxygen or sulphur, each of which is unsubstituted or substituted in the heterocyclyl moiety by identical or different substituents, suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio; $R^4$ and $R^5$ independently of one another furthermore represent benzyl, phenylethyl, phenylpropyl, phenylbutyl, phenylpentyl, phenylhexyl, phenylheptyl, phenylcyanomethyl, phenylcyanoethyl, phenylcyanopropyl, benzoyl, phenyl or naphthyl, and in each case unsubstituted or substituted by identical or different substituents, suitable phenyl substituents in each case being: fluorine, chlorine, bromine, hydroxyl, cyano, nitro, methyl, ethyl, n- or i-propyl, n-, i-, s-or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl or phenoxy, or $R^4$ and $R^5$ together with the nitrogen atom to which they are bonded can also represent a heterocycle of the formula

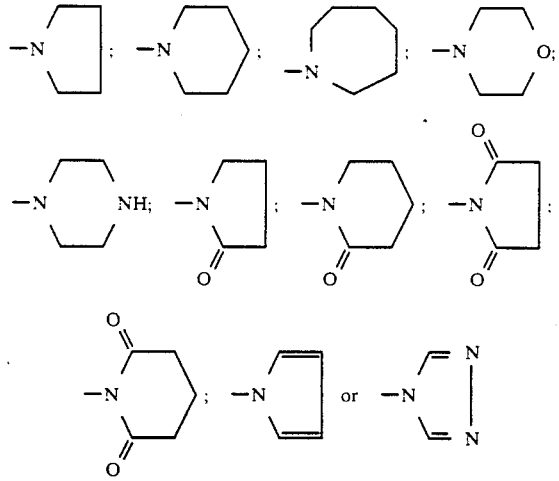

which is unsubstituted or substituted by identical or different substituents, suitable substituents in each case being; methyl, ethyl, n- or i-propyl, chlorine or trifluoromethyl.

3. A process according to claim 1, wherein the reaction is carried out in the presence of a solvent.

4. A process according to claim 1, wherein the reaction is carried out in the presence of an acid acceptor.

5. A process according to claim 1, wherein the reaction is carried out at temperatures from 0° C. to 150° C.

6. A process according to claim 1, wherein between 0.5 and 1.5 moles of oxamohydrazide are employed per mole of chloroformadine hydrochloride.

7. A process according to claim 1, wherein between 0.5 and 1.5 moles of oxamohydrazide and 1 to 5 mole equivalents of an acid acceptor are employed per mole of chloroformamidine hydrochloride.

* * * * *

UNITED STATES PATENT AND TRADEMARK OFFICE
CERTIFICATE OF CORRECTION

PATENT NO. : 5,051,517

DATED : September 24, 1991

INVENTOR(S) : Kurt Findeisen, et al.

It is certified that error appears in the above-identified patent and that said Letters Patent is hereby corrected as shown below:

Col. 16, line 28   After " having " insert -- 1 --

Col. 17, line 28   After " and " insert -- 1 --

Signed and Sealed this

Eighteenth Day of May, 1993

Attest:

MICHAEL K. KIRK

Attesting Officer

Acting Commissioner of Patents and Trademarks